United States Patent [19]

Hommann

[11] Patent Number: 4,644,937
[45] Date of Patent: Feb. 24, 1987

[54] MOUTH AND TOOTH SPRAY APPARATUS

[75] Inventor: Edgar Hommann, Grossaffoltern, Switzerland

[73] Assignee: Gimelli & Co. AG, Switzerland

[21] Appl. No.: 606,219

[22] Filed: May 2, 1984

[30] Foreign Application Priority Data

May 3, 1983 [DE] Fed. Rep. of Germany ....... 3316016

[51] Int. Cl.$^4$ .............................................. A61H 9/00
[52] U.S. Cl. .................... 128/66; 128/62 A; 433/80
[58] Field of Search .................. 132/84 R; 128/62 A, 128/66; 15/22 A, 22 R; 433/80; 222/321, 402.24

[56] References Cited

U.S. PATENT DOCUMENTS 4,442,830  4/1984  Markau .............................. 128/62 A

*Primary Examiner*—Robert Peshock
*Attorney, Agent, or Firm*—Wegner & Bretschneider

[57] ABSTRACT

In a mouth- and tooth-spray apparatus, the energy supply to an electric motor in the apparatus base is supplies by means of a rechargeable battery of an electric toothbrush. For this purpose, the electric toothbrush is to be inserted into a toothbrush receiver of the apparatus base, exactly as into a conventional charging device.

By means of this design, the mouth- and toothspray apparatus requires no high voltage power supply connections. Instead, it is exclusively operated with low voltage.

4 Claims, 4 Drawing Figures

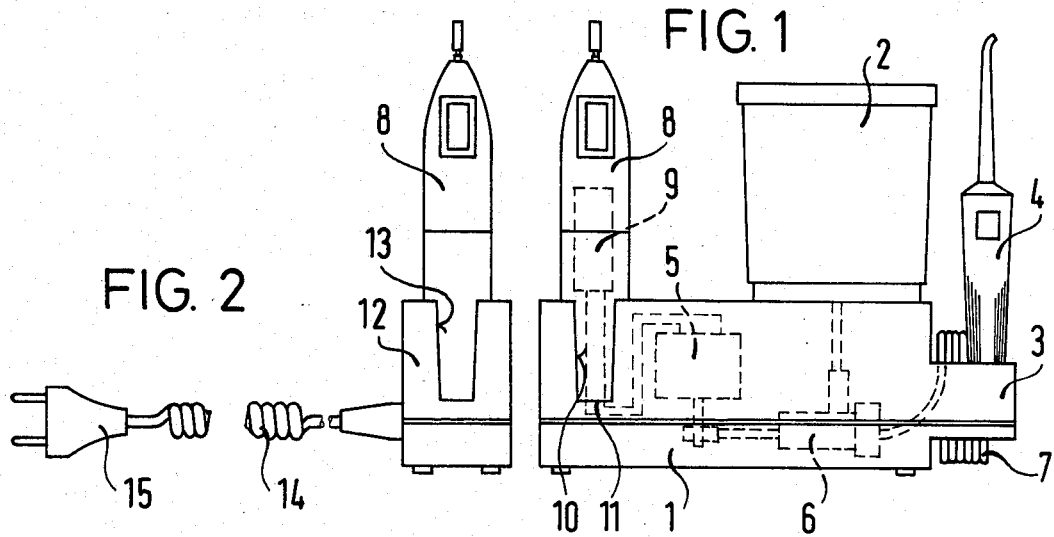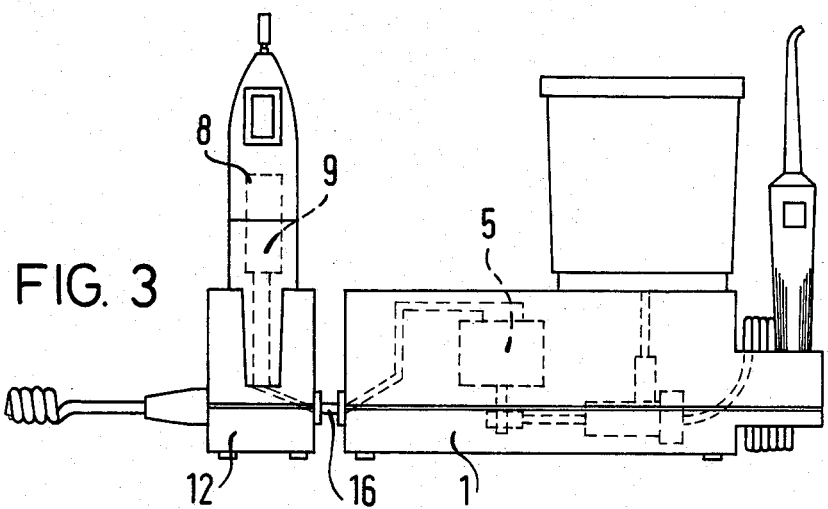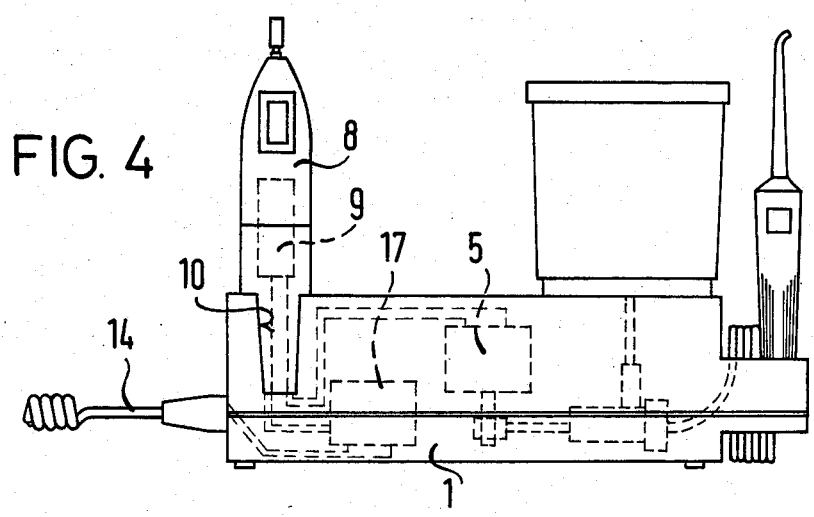

4,644,937

MOUTH AND TOOTH SPRAY APPARATUS

This invention relates to a mouth- and tooth-spray apparatus with a water pump driven by an electric motor. Such mouth- and tooth-spray apparatuses are increasingly used in the private sphere and are generally known.

The hitherto usual mouth- and tooth-spray apparatuses are driven either hydraulically from the main water supply or electrically from an electric supply. Due to their functional capability, only the electrically driven mouth- and tooth-spray apparatuses have gained wide acceptance. Unfortunately, fatal accidents due to electrical equipment still continually occur, particularly in bathrooms, in which such mouth- and tooth-spray apparatuses are predominatly used, since the users of electrical apparatus are not aware of the danger from electric current. A mouth- and tooth-spray apparatus connected to the electrical supply mains can, e.g., fall into a washbasin full of water with possibly fatal consequences.

Because of such dangers, the installation of electrical outlets in bathrooms has already been generally prohibited in some countries. No electrically operated electrical appliances, such as hair dryers or mouth- and tooth-spray apparatuses, can then be used in the bathroom. Particularly for mouth- and tooth-spray apparatuses, however, use in the bathroom is desirable, since such appliances must be used over the washbasin.

SUMMARY OF THE INVENTION

The object of the invention is to develop a mouth- and tooth spray apparatus which is as safe as possible from accidents with electric current.

This problem is solved according to the invention in that the electric motor is a low-voltage motor, the terminals of which can be connected to rechargeable battery provided in an electric toothbrush.

The battery of the usual electric toothbrush operates with an electrical voltage of 2.4 volts. Accidents by contact with current-bearing parts are thus excluded. Since the electric motor of a mouth- and tooth-spray apparatus must have a relatively high power consumption, it would be insufficient to connect this with the secondary winding of the transformer of the charging device for the toothbrush. However, the battery is able to deliver the required current for a short period, and in doing so becomes discharged relatively quickly.

Since the battery of the electric toothbrush is obligatorily recharged, however, as soon as the toothbrush, when no longer in use, is placed in the charging device, this demand on the battery represents no disadvantage.

An advantageous embodiment of the invention consists in that the apparatus base has a toothbrush receiver which is designed exactly like the toothbrush receiver of a charging device for the electric toothbrush and which has a voltage takeoff, connected to the electric motor, to take electrical energy from the toothbrush battery. This design is particularly simple and practical for manipulation. It is only necessary to place the electric toothbrush, which is necessarily required for cleaning the teeth, in the toothbrush receiver of the mouth- and tooth-spray apparatus, in order to have an energy source for its electric motor. The mouth- and tooth-spray apparatus according to the invention can therefore be used in a room in which no high voltage connection is provided. It is thus absolutely safe from accidents with electric current.

An alternative, likewise safe, embodiment is characterized by the apparatus base being connected via a low-voltage cable to an electric charging device for an electric toothbrush, and this low-voltage cable is connected in the charging device, with the toothbrush inserted, to the battery of the toothbrush. It also offers the advantage that no high voltage is present in the mouth- and tooth-spray apparatus. The charging device itself, which is operated by high voltage and is fixed to the wall, offers the possibility of supplying from the battery, by means of a connecting cable, the low-voltage current for the motor of the mouth- and tooth-spray apparatus, so that here also no source of danger for the user arises if the apparatus falls into the washbasin.

It is also suitable for the mouth- and tooth-spray apparatus to be combined with the charging device into a single unit. Such a combined arrangement can be produced at a particularly favorable cost. It offers a high level of safety against electrical accidents, since the parts connected to the high voltage can easily be watertightly encapsulated, while only low voltage is present in the remaining parts which are not to be encapsulated.

BRIEF DESCRIPTION OF THE DRAWINGS

The invention permits numerous embodiments. To explain its basic principles, three embodiments are described below and shown in the drawing, wherein:

FIG. 1 is a schematic depiction of a first embodiment of a mouth- and tooth-spray apparatus according to the invention;

FIG. 2 schematically shows a conventional charging device with an electric toothbrush, which can be inserted in the mouth- and tooth-spray apparatus according to the invention.

FIG. 3 schematically shows a second embodiment of a mouth- and tooth-spray apparatus according to the invention, electrically connected to the charging device of an electric toothbrush;

FIG. 4 is a schematic depiction of a third embodiment of a mouth- and tooth-spray apparatus according to the invention.

DESCRIPTION OF THE PREFERRED EMBODIMENTS

The mouth- and tooth-spray apparatus shown in FIG. 1 has an apparatus base 1, on which stands a water container 2. A handpiece 4 with spray nozzle is arranged in a mounting 3 near the water container 2. In use of the mouth- and tooth-spray apparatus, an electric motor 5 shown dashed, drives a pump 6, likewise shown dashed, so that water can flow from the water container 2 via the tube 7 into the handpiece 4 and thence can spray via the spray nozzle.

It is essential for the invention that the electric motor 5 is a low-voltage motor. Furthermore the manner in which this electric motor is supplied with electrical energy is essential for the invention. For this electric supply, use is made of a conventional electric toothbrush 8 with a rechargeable battery 9. The electric toothbrush stands, exactly as in the charging device, in a toothbrush receiver 10 of the apparatus base 1. This toothbrush receiver 10 has a voltage takeoff 11, from which electrical energy can flow from the battery 9 to the electric motor 5 as soon as the toothbrush 8 is placed in the toothbrush receiver 10.

An electric switch (not shown) can of course be provided between the voltage takeoff 11 and the electric motor 5, so that the mouth- and tooth-spray apparatus can be switched off even when the toothbrush 8 is put down in the toothbrush receiver 10. The switch can be located in the mounting 3 and be of a type that will switch off the current when the handpiece 4 is placed in the mounting 3.

FIG. 2 shows a conventional charging device 12 with a toothbrush receiver 13. This charging device 12 has a power cable 14 with a plug 15 and can thereby be connected to a high voltage electric supply. The electric toothbrush 8 stands in the toothbrush receiver 13. This toothbrush 8 is to be pulled out of the toothbrush receiver 13 and inserted in the toothbrush receiver 10 of the mouth- and tooth-spray apparatus when the mouth- and tooth-spray apparatus according to the invention is to be used.

In the embodiment according to FIG. 3, the apparatus base 1 of the mouth- and tooth-spray apparatus has no toothbrush receiver 10. Instead of this, a low-voltage cable 16 runs from the apparatus base 1 to the charging device 12. This charging device is designed such that current from the battery 9 of the toothbrush 8 standing in the charging device 12 can flow through the low-voltage cable 16 to the electric motor 5 in the apparatus base 1.

FIG. 4 shows an embodiment of a mouth-and tooth-spray apparatus, in which this is combined with the charging device of an electric toothbrush. For this, the apparatus base 1, exactly as in the embodiment according to FIG. 1, has a toothbrush receiver 10 for mounting the toothbrush 8; however, it has, additionally, in the base a watertight potted transformer 17, by which the high voltage from the mains cable 14 is transformed down, and from which the battery 9 in the toothbrush 8 is supplied with electrical energy. The electric motor 5 is again a low-voltage motor, which obtains electrical energy exclusively from the battery 9 in the toothbrush 8.

Finally, it should be noted that there are two kinds of rechargeable toothbrushes. One kind has two contact pins and is charged with direct current of 1.2-2.4 volts. In the other toothbrushes, charging takes place inductively, i.e., a secondary circuit is located in the toothbrush and produces the required charging current.

With the first kind of toothbrush, the current to operate the motor of the mouth- and tooth-spray apparatus can be taken out of the battery at the contact pins which are used for charging. In toothbrushes with inductive charging, two contact points have to be brought out, in order to be able to take current from the battery.

I claim:

1. Mouth- and tooth-spary apparatus comprising an apparatus base, a water container mounted on said base, a handpiece containing a spray nozzle removably mounted on said base, said base containing an electric motor and a water pump driven thereby, said electric motor being a low-voltage motor, the terminals of which are detachably connected to a rechargeable battery disposed in an electric toothbrush, said pump being operatively connected between said container and said handpiece to pump water from said container to said nozzle.

2. Mouth- and tooth-spray apparatus according to claim 1, wherein the apparatus base further contains receiver means for the electric toothbrush and contact means disposed in the receiver means and connected to the electric motor to take electrical energy out of the battery of the toothbrush.

3. Mouth- and toothspray apparatus according to 1, wherein the apparatus base is connected via a low-voltage cable to an electric charging device for an electric toothbrush, and this low-voltage cable is connected in the charging device, with the toothbrush inserted, to the battery of the toothbrush.

4. Mouth- and tooth-spray appartus according to claim 1, further comprising an electrical charging device for an electric tootbrush arranged in the apparatus base.

* * * * *